US012239293B2

(12) United States Patent
Russell

(10) Patent No.: US 12,239,293 B2
(45) Date of Patent: Mar. 4, 2025

(54) ENDOSCOPE FOR SENSING TROCARS, COMPATIBLE CANNULAS, INSTRUMENTS AND ACCESSORIES

(71) Applicant: Verb Surgical Inc., Santa Clara, CA (US)

(72) Inventor: Geoffrey Robert Russell, San Jose, CA (US)

(73) Assignee: Verb Surgical Inc., Santa Clara, CA (US)

( * ) Notice: Subject to any disclaimer, the term of this patent is extended or adjusted under 35 U.S.C. 154(b) by 405 days.

(21) Appl. No.: 17/062,433

(22) Filed: Oct. 2, 2020

(65) Prior Publication Data

US 2022/0104695 A1    Apr. 7, 2022

(51) Int. Cl.
| | |
|---|---|
| *A61B 1/018* | (2006.01) |
| *A61B 1/00* | (2006.01) |
| *A61B 17/00* | (2006.01) |
| *A61B 17/34* | (2006.01) |
| *A61B 34/30* | (2016.01) |

(52) U.S. Cl.
CPC .......... *A61B 1/018* (2013.01); *A61B 1/00006* (2013.01); *A61B 1/00016* (2013.01); *A61B 17/00234* (2013.01); *A61B 17/3421* (2013.01); *A61B 17/3478* (2013.01); *A61B 34/30* (2016.02)

(58) Field of Classification Search
CPC . A61B 1/018; A61B 1/00006; A61B 1/00016; A61B 17/00234; A61B 17/3421; A61B 17/3478; A61B 34/30; A61B 1/00059; A61B 1/00154; A61B 90/361; A61B 90/98

See application file for complete search history.

(56) References Cited

U.S. PATENT DOCUMENTS

| | | | | |
|---|---|---|---|---|
| 8,720,448 | B2 * | 5/2014 | Reis ....................... | A61B 34/30 606/130 |
| 9,980,778 | B2 * | 5/2018 | Ohline .................. | A61B 1/005 |
| 10,441,132 | B2 * | 10/2019 | Kikuchi ............. | A61B 1/00154 |
| 10,765,487 | B2 * | 9/2020 | Ho ......................... | A61B 34/71 |
| 2001/0051766 | A1 * | 12/2001 | Gazdzinski ............ | A61B 10/02 606/1 |

(Continued)

*Primary Examiner* — Anh T Nguyen
*Assistant Examiner* — Shankar Raj Ghimire
(74) *Attorney, Agent, or Firm* — Aikin & Gallant, LLP

(57) ABSTRACT

Disclosed are systems and methods for an endoscope or other surgical instruments to automatically sense when it's placed inside or outside of a trocar or a cannula. Operational setting of the endoscope may be adjusted as a function of the detected environmental condition to improve the function of the endoscope and the safety of a surgical procedure. The endoscope may include a sensor to sense a tag embedded in a trocar or cannula. The endoscope may transmit sensing information to a controller of a surgical robotic system to indicate that the endoscope has been inserted into the trocar or cannula. The controller may generate configuration information corresponding to the sensed state. The controller may transmit the configuration information to the endoscope to configure the endoscope to operate in the state. In another aspect, the endoscope may wirelessly communicate with another surgical instrument to receive operational information from the surgical instrument.

21 Claims, 13 Drawing Sheets

(56) References Cited

U.S. PATENT DOCUMENTS

| | | | | |
|---|---|---|---|---|
| 2004/0176683 | A1* | 9/2004 | Whitin | A61B 5/068 |
| | | | | 600/117 |
| 2006/0187044 | A1* | 8/2006 | Fabian | A61B 5/06 |
| | | | | 340/572.1 |
| 2007/0249901 | A1* | 10/2007 | Ohline | A61B 5/065 |
| | | | | 600/117 |
| 2009/0184825 | A1* | 7/2009 | Anderson | G06Q 10/087 |
| | | | | 340/572.1 |
| 2013/0053643 | A1* | 2/2013 | Yoshida | A61B 1/126 |
| | | | | 600/114 |
| 2015/0119638 | A1* | 4/2015 | Yu | A61B 1/018 |
| | | | | 600/102 |
| 2015/0216610 | A1* | 8/2015 | Augustine | G06K 19/08 |
| | | | | 235/492 |
| 2016/0213364 | A1* | 7/2016 | Inoue | A61B 1/008 |
| 2016/0213436 | A1* | 7/2016 | Inoue | A61B 34/37 |
| 2016/0302653 | A1* | 10/2016 | Inoue | G01C 3/08 |
| 2017/0086906 | A1* | 3/2017 | Tsuruta | A61B 1/018 |
| 2017/0340396 | A1* | 11/2017 | Romo | B25J 9/1694 |
| 2018/0289431 | A1* | 10/2018 | Draper | A61B 34/20 |
| 2019/0000568 | A1* | 1/2019 | Connolly | A61B 34/71 |
| 2019/0262086 | A1* | 8/2019 | Connolly | A61B 5/062 |
| 2020/0405411 | A1* | 12/2020 | Draper | A61B 1/00149 |
| 2022/0046166 | A1* | 2/2022 | Holmstrom | A61B 1/317 |

* cited by examiner

ENDOSCOPE FOR SENSING TROCARS, COMPATIBLE CANNULAS, INSTRUMENTS AND ACCESSORIES

TECHNICAL FIELD

The subject technology of the present disclosure generally relates to robotics and surgical systems, and more specifically, to systems, devices, and techniques for an endoscope to automatically sense when it is placed in a trocar or cannula or to sense other instruments and accessories used during a minimally-invasive surgical procedure including one enabled by a robotically-assisted surgical system.

BACKGROUND

Minimally-invasive surgery, MIS, such as laparoscopic surgery, uses techniques that are intended to reduce tissue damage during a surgical procedure. Laparoscopic procedures typically call for creating a number of small incisions in the patient, e.g., in the abdomen, through which several surgical tools such as an endoscope, a scalpel, a grasper, and a needle, are then inserted into the patient. A gas is injected into the abdomen which insufflates the abdomen thereby providing more space around the tips of the tools, making it easier for the surgeon to see (via the endoscope) and manipulate tissue at the surgical site. MIS can also be performed using a robotic system in which the surgical tools are operatively attached to the distal ends of robotic arms, and a control system actuates the arm and its attached tool so that the latter mimics the movements and tool specific commands of a user input device (UID) as the latter is being manipulated by a surgeon in their hand.

During an initial insertion of an endoscope through the small incision made in the patient, the endoscope is typically assembled in an optical trocar that includes a seal cartridge called a cannula and an optical obturator. A surgeon may insert the optical trocar through the small incision and may use the optical obturator to puncture through successive tissue layers of the abdominal or thoracic cavity until the endoscope is placed at the proper surgical site. During this initial optical entry phase, the field of view of the endoscope may be obstructed by the geometry of the optical obturator. The result is compromised visualization during optical entry, especially for a 3D endoscope that uses stereo images from two cameras to provide depth perception. After optical entry, the endoscope and the optical obturator may be retracted from the cannula while leaving the cannula in place. The surgeon may dispose of the optical obturator and then re-insert the endoscope back into the cannula until it reaches the proper surgical site again. While the endoscope is retracted out of the cannula and before re-insertion, the endoscope may continue to operate even though it's outside of the patient's body, resulting in inadvertent recording of personal health information of the patient and potentially running afoul of regulations intended to protect the privacy of the patient. While manual intervention or machine learning algorithm may be implemented to remove recorded segments of videos captured when the endoscope is external to the patient, these measures incur extra time and expenses.

SUMMARY

Systems and methods are disclosed for an endoscope to automatically sense when it's placed inside or outside of a trocar or cannula. Operational setting and configuration of the endoscope may be adjusted as a function of the detected environmental condition to improve the function of the endoscope and the safety of the surgical procedure. For example, when the endoscope senses that it is placed inside an optical trocar, a control system may determine that the endoscope will be used for optical entry and may adjust the endoscope's field of view to correct the obstructed visualization caused by the geometry of the optical obturator. Alternatively, when the endoscope senses that it is outside of a cannula, the endoscope may stop capturing the video or a video recording system may use the sensed information to automatically segment the video to remove the portion recorded when the endoscope is external to the patient. Endoscope light source may produce a significant amount of heat when the tip is in contact with a surgical drape or patient skin, causing safety concerns. In one embodiment, when the endoscope is detected as being outside of the cannula, the control system may automatically turn off the endoscope light source to prevent patient burns, temporary blinding of bedside assistants, or operating room fires.

In one aspect, the endoscope may sense a procedure-specific cannula into which it has been inserted. The endoscope or the control system may receive identification information from the procedure-specific cannula and may configure the endoscope with settings tailored for the specific procedure detected. For example, the control system may adjust the visualization setting or may drive the robotic arms attached to the endoscope or other surgical instruments to the pose specific to the procedure. In one embodiment, the endoscope may embed a sensor that is capable of reading passive radio frequency identification (RFID) tags embedded in trocars or cannulas. In other embodiments, the endoscope may use other types of near-field communication (NFC) with passive or active tags or may use links such as Bluetooth to sense and read information from the trocars or cannulas.

In another aspect, the endoscope in a cannula may wirelessly communicate with a laparoscopic instrument in another cannula to form a mesh network to receive operational information or environmental condition from the laparoscopic instrument or the other cannula. The endoscope may transmit the received information to a control system for data processing. For example, the endoscope may receive insufflation pressure data from a pressure sensor on a laparoscopic instrument or cannula and may relay the pressure information to the control system for monitoring. In one embodiment, the endoscope may receive feedback information from the control system to adjust the configuration of the endoscope or the laparoscopic instrument and may relay the feedback information to the laparoscopic instrument. For example, the endoscope may receive feedback information to adjust its visualization setting and the firing energy of a cautery instrument that may generate smoke when the endoscope is used in conjunction with the cautery instrument. The endoscope may relay the feedback information containing configuration setting for the cautery instrument to the cautery instrument for it to adjust its firing energy.

A method for configuring a surgical instrument is disclosed. The method may be performed by a controller of a surgical robotic system. The method includes the controller receiving sensing information from the surgical instrument indicating that the surgical instrument is inserted into a cannula or a trocar. The method also includes the controller generating configuration information of the surgical instrument based on the received sensing information. The configuration information is used to configure the surgical instrument to operate in a state corresponding to when it is in the cannula or the trocar. The method further includes the controller transmitting the configuration information to the surgical instrument to configure the surgical instrument to operate in the corresponding state.

A surgical instrument of a surgical robotic system is disclosed. The surgical instrument includes a sensor and a processor. The sensor may sense a tag embedded in a cannula or a trocar. The processor may first initialize the surgical instrument to an initial state. The processor may detect a sensing signal that is generated when the sensor senses the tag embedded in the cannula or the trocar. The processor may transmit sensing information to a controller of the surgical robotic system in response to the sensing signal. The sensing information is used to indicate that the surgical instrument has been inserted into the cannula or the trocar. The processor may receive configuration information from the controller. The configuration information is used to configure the surgical instrument to operate in a state corresponding to when it is in the cannula or the trocar. The processor may then configure the surgical instrument to operate in the corresponding state.

BRIEF DESCRIPTION OF THE DRAWINGS

The accompanying drawings are provided together with the following description of various aspects and embodiments of the subject technology for a better comprehension of the invention. The drawings and the embodiments are illustrative of the invention, and are not intended to limit the scope of the invention. It is understood that a person of ordinary skill in the art may modify the drawings to generate drawings of other embodiments that would still fall within the scope of the invention. In the drawings, like reference numerals refer to like parts.

DETAILED DESCRIPTION

Figure 1:
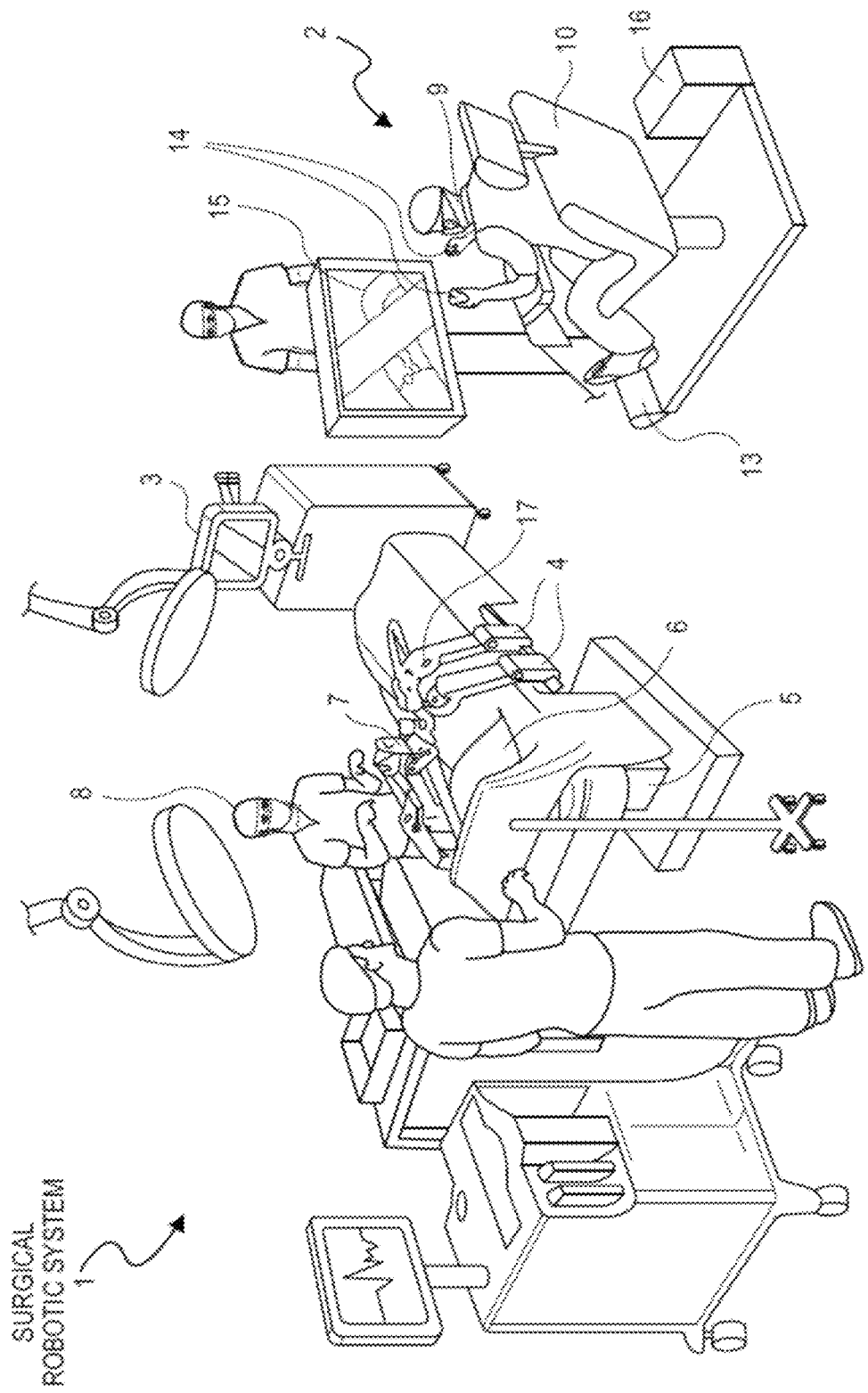
FIG. 1 is a pictorial view of an example surgical robotic system in an operating arena in which automatic sensing by an endoscope may be implemented, in accordance with aspects of the subject technology described herein.

Examples of various aspects and variations of the subject technology are described herein and illustrated in the accompanying drawings. The following description is not intended to limit the subject technology to these embodiments, but rather to provide specific details for a thorough understanding of, and to enable a person skilled in the art to make and use, the subject technology. In some instances, structures and components are shown in block diagram form in order to avoid obscuring the concepts of the subject technology.

In light of the problems described in the background section, it is desirable for an endoscope to sense its operating environment within a surgical robotic system to allow the endoscope to adjust its operating configuration accordingly. Disclosed are systems, methods, and techniques for the endoscope to sense when it is placed in a trocar or cannula so as to automatically configure the endoscope for use in a surgical procedure. In particular, the endoscope may sense its placement in a cannula associated with a specific procedure so as to be automatically configured with a setting specific to the procedure. Conversely, the endoscope may sense when it is outside of, or retracted from, the trocar or cannula so as to automatically switch to a configuration associated with a non-operational mode. Automatic sensing of the operating environment by the endoscope may extend to sensing by the endoscope of a surgical instrument or accessory used in conjunction with the endoscope or the operating condition of the surgical instrument or accessory. The endoscope may transmit information on the sensed operating environment to a control system for processing. The control system may process the information to configure the endoscope to operate safely and effectively in the operating environment or may use the endoscope as a relay to configure the surgical instrument or accessory.

In one aspect, the endoscope has a reader that is capable of reading a RFID tag that is embedded in an optical obturator of a trocar. When the endoscope is inserted into the trocar, the reader senses the RFID of the optical obturator to determine that the endoscope will be used with the trocar for optical entry. The configuration setting of the endoscope may be adjusted automatically by the endoscope or by a control system connected to the endoscope to optimize the visual experience for optical entry, for example by applying image cropping, zooming, or color preset to correct the obstructed field of view caused by the geometry of the optical obturator.

In one embodiment, when the endoscope is inserted into a cannula that embeds within its cannula seal a RFID associated with a specific procedure, the reader senses the RFID to learn that the endoscope will be used for the specific procedure. The configuration setting of the endoscope may be adjusted automatically to improve the safety and effectiveness of the endoscope for the specific procedure, for example by adjusting color tuning, electrosurgical setting, etc. In one embodiment, when a button on the endoscope is pushed, a robotic arm attached to the endoscope may be driven to an initial pose of the specific procedure.

In one embodiment, when the endoscope is inserted into a cannula, the reader senses the RFID of the cannula to determine that the direction of motion of the endoscope is into the patient's body or that the endoscope is inside of the patient's body. The endoscope may be automatically configured to start capturing videos with the endoscope light turned on. Conversely, when the endoscope is retracted from the cannula, the reader senses the RFID to determine that the direction of motion of the endoscope is away from the patient's body or that the endoscope is outside of the patient's body. The endoscope may be automatically configured to turn off video capture or a video recording system may use the sensed information to automatically segment the video to remove the portion when the endoscope is external to the patient. The endoscope light may also be automatically turned off to prevent patient burns, blinding of bedside assistants, or operating room fires when the tip of the retracted endoscope may be in contact with a surgical drape or patient skin.

In another aspect, the endoscope in a cannula may wirelessly communicate with a laparoscopic instrument in another cannula to form a mesh network to receive operational information or environmental condition from the laparoscopic instrument or the other cannula. The other cannula may have a sensor to read an RFID embedded in a laparoscopic instrument or to sense the environmental condition such as the insufflation pressure inside the patient's body. The other cannula may wirelessly transmit identification information of the laparoscopic instrument or the sensed environmental condition to the endoscope. In one embodiment, the endoscope may transmit its own sensed information and the information received from the other cannula to the control system for processing. The control system may process the information to configure the endoscope to work in conjunction with the laparoscopic instrument.

In one embodiment, the control system may generate configuration setting for the laparoscopic instrument based on the sensed information. The endoscope may transmit the configuration setting for the laparoscopic instrument to the other cannula. In one embodiment, the endoscope may generate the configuration setting for the laparoscopic instrument based on feedback information from the control system such as visual feedback of processed images, information on the surgical procedure, sensed data from other sensors or cannulas, etc. The control system or the endoscope may configure the laparoscopic instrument to operate in conjunction with the endoscope. In one embodiment, the laparoscopic instrument may be configured to adjust its energy setting for the surgical procedure identified from the sensed information.

FIG. 1 is a pictorial view of an example surgical robotic system 1 in an operating arena in which automatic sensing by an endoscope may be implemented, in accordance with aspects of the subject technology. The robotic system 1 includes a user console 2, a control tower 3, and one or more surgical robotic arms 4 at a surgical robotic platform 5, e.g., a table, a bed, etc. The arms 4 may be mounted to a table or bed on which the patient rests as shown in the example of FIG. 1, or they may be mounted to a cart separate from the table or bed. The system 1 can incorporate any number of devices, tools, or accessories used to perform surgery on a patient 6. For example, the system 1 may include one or more surgical tools 7 used to perform surgery. A surgical tool 7 may be an end effector or an endoscope that is attached to a distal end of a surgical arm 4, for executing a surgical procedure.

Each surgical tool 7 may be manipulated manually, robotically, or both, during the surgery. For example, the surgical tool 7 may be a tool used to enter, view, or manipulate an internal anatomy of the patient 6. In one aspect, the surgical tool 7 is a grasper such as wrist jaws that can grasp tissue of the patient. The surgical tool 7 may be configured to be controlled manually by a bedside operator 8, robotically via actuated movement of the surgical robotic arm 4 to which it is attached, or both. The robotic arms 4 are shown as being table-mounted but in other configurations the arms 4 may be mounted to a cart, the ceiling or a sidewall, or to another suitable structural support.

A remote operator 9, such as a surgeon or other human operator, may use the user console 2 to remotely manipulate the arms 4 and their attached surgical tools 7, e.g., referred to here as teleoperation. The user console 2 may be located in the same operating room as the rest of the system 1 as shown in FIG. 1. In other environments however, the user console 2 may be located in an adjacent or nearby room, or it may be at a remote location, e.g., in a different building, city, or country. The user console 2 may comprise a seat 10, foot-operated controls 13, one or more handheld user input devices, UID 14, and at least one user display 15 that is configured to display, for example, a view of the surgical site inside the patient 6. In the example user console 2, the remote operator 9 is sitting in the seat 10 and viewing the user display 15 while manipulating a foot-operated control 13 and a handheld UID 14 in order to remotely control the arms 4 and the surgical tools 7 that are mounted on the distal ends of the arms 4.

In some variations, the bedside operator 8 may operate the system 1 in an "over the bed" mode in which the beside operator 8 (user) is at a side of the patient 6 and is simultaneously manipulating a robotically-driven tool (an end effector that is attached to the arm 4) with a handheld UID 14 held in one hand, and a manual laparoscopic tool in another hand. For example, the bedside operator's left hand may be manipulating the handheld UID 14 to control a robotically-driven tool, while the bedside operator's right hand may be manipulating a manual laparoscopic tool. In this particular variation of the system 1, the bedside operator 8 can perform both robotic-assisted minimally invasive surgery and manual laparoscopic surgery on the patient 6.

During an example procedure (surgery), the patient 6 is prepped and draped in a sterile fashion to achieve anesthesia. Initial access to the surgical site may be performed manually while the arms of the robotic system 1 are in a stowed configuration or withdrawn configuration (to facilitate access to the surgical site.) Once access is completed, initial positioning or preparation of the robotic system 1 including its arms 4 may be performed. Next, the surgery proceeds with the remote operator 9 at the user console 2 utilising the foot-operated controls 13 and the UIDs 14 to manipulate the various end effectors and perhaps an imaging system to perform the surgery. Manual assistance may also be provided at the procedure bed or table by sterile-gowned bedside personnel, e.g., the bedside operator 8, who may perform tasks such as retracting tissues, performing manual repositioning, and tool exchange upon one or more of the robotic arms 4. Non-sterile personnel may also be present to assist the remote operator 9 at the user console 2. When the procedure or surgery is completed, the system 1 and the user console 2 may be configured or set in a state to facilitate post-operative procedures such as cleaning or sterilization and healthcare record entry or printout via the user console 2.

In one embodiment, the remote operator 9 holds and moves the UID 14 to provide an input command to move a robot arm actuator 17 in the robotic system 1. The UID 14 may be communicatively coupled to the rest of the robotic system 1, e.g., via a console computer system 16. The UID 14 can generate spatial state signals corresponding to movement of the UID 14, e.g. position and orientation of the handheld housing of the UID, and the spatial state signals may be input signals to control a motion of the robot arm actuator 17. The robotic system 1 may use control signals derived from the spatial state signals, to control proportional motion of the actuator 17. In one embodiment, a console processor of the console computer system 16 receives the spatial state signals and generates the corresponding control signals. Based on these control signals, which control how the actuator 17 is energized to move a segment or link of the arm 4, the movement of a corresponding surgical tool that is attached to the arm may mimic the movement of the UID 14.

The surgical robotic system 1 may include several UIDs 14, where respective control signals are generated for each UID that control the actuators and the surgical tool (end effector) of a respective arm 4. For example, the remote operator 9 may move a first UID 14 to control the motion of an actuator 17 that is in a left robotic arm, where the actuator responds by moving linkages, gears, etc., in that arm 4. Similarly, movement of a second UID 14 by the remote operator 9 controls the motion of another actuator 17, which in turn moves other linkages, gears, etc., of the robotic system 1. The robotic system 1 may include a right arm 4 that is secured to the bed or table to the right side of the patient, and a left arm 4 that is at the left side of the patient. An actuator 17 may include one or more motors that are controlled so that they drive the rotation of a joint of the arm 4 to, for example, change, relative to the patient, an orientation of an endoscope or a grasper of the surgical tool 7 that is attached to that arm. Motion of several actuators 17 in the same arm 4 can be controlled by the spatial state signals generated from a particular UID 14. The UIDs 14 can also control motion of respective surgical tool graspers. For example, each UID 14 can generate a respective grip signal to control motion of an actuator, e.g., a linear actuator, which opens or closes jaws of the grasper at a distal end of surgical tool 7 to grip tissue within patient 6.

In some aspects, the communication between the platform 5 and the user console 2 may be through a control tower 3, which may translate user commands that are received from the user console 2 (and more particularly from the console computer system 16) into robotic control commands and transmit them to the arms 4 on the robotic platform 5. The control tower 3 may also transmit status and feedback from the platform 5 back to the user console 2. The communication connections between the robotic platform 5, the user console 2, and the control tower 3 may be via wired and/or wireless links, using any suitable ones of a variety of data communication protocols. Any wired connections may be optionally built into the floor and/or walls or ceiling of the operating room. The robotic system 1 may provide video output to one or more displays, including displays within the operating room as well as remote displays that are accessible via the Internet or other networks. The video output (video feed) may also be encrypted to ensure privacy and all or portions of the video output may be saved to a server or electronic healthcare record system.

Figure 2:
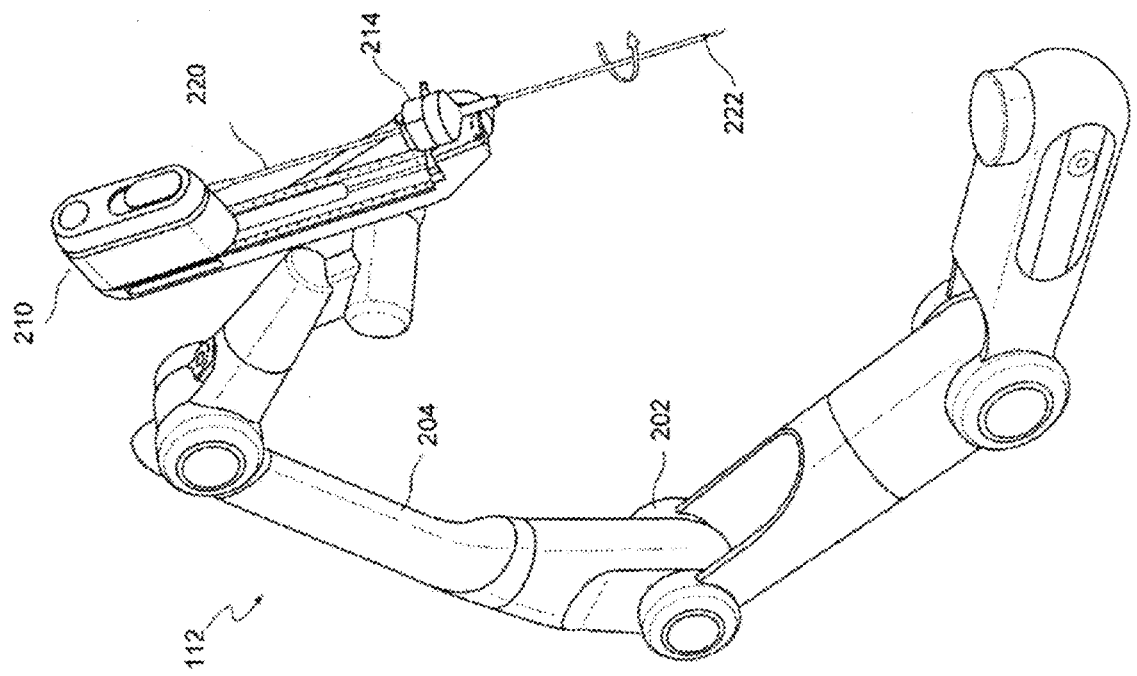
FIG. 2 is a schematic diagram illustrating one exemplary design of a robotic arm of the surgical robotic system, a tool drive, and a cannula loaded with a robotic surgical tool, in accordance with aspects of the subject technology described herein.

FIG. 2 is a schematic diagram illustrating one exemplary design of a robotic arm 112 of surgical robotic system 1, a tool drive 210, and a cannula 214 loaded with a robotic surgical tool 220, in accordance with aspects of the subject technology. As shown in FIG. 2, the example surgical robotic arm 112 may include a plurality of links (e.g., a link 202) and a plurality of actuated joint modules (e.g., a joint 204) for actuating the plurality of links relative to one another. The joint modules may include various types, such as a pitch joint or a roll joint, which may substantially constrain the movement of the adjacent links around certain axes relative to others. Also shown in the exemplary design of FIG. 2 is a tool drive 210 attached to the distal end of the robotic arm 112. The tool drive 210 may include a cannula 214 coupled to its end to receive and guide a surgical instrument 220 (e.g., endoscopes, staplers, etc.). The surgical instrument (or "tool") 220 may include an end effector 222 at the distal end of the tool. The plurality of the joint modules of the robotic arm 112 can be actuated to position and orient the tool drive 210, which actuates the end effector 222 for robotic surgeries.

Figure 3A:
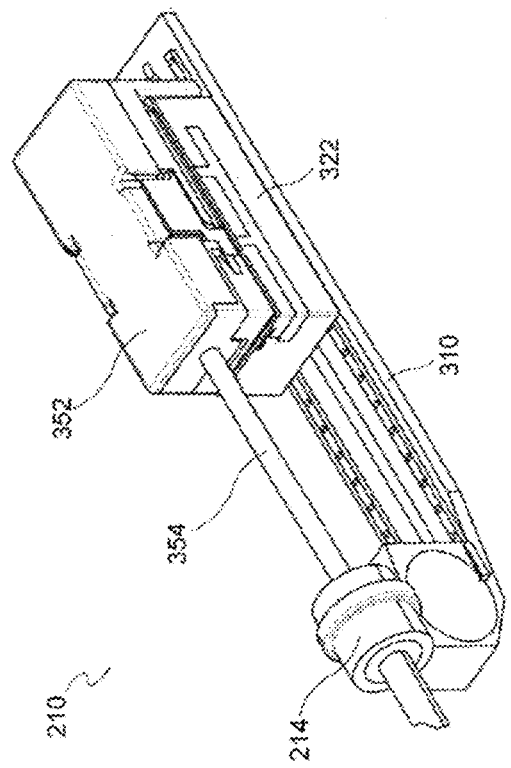
FIGS. 3A and 3B are schematic diagrams illustrating an exemplary tool drive with and without a loaded tool, respectively, in accordance with aspects of the subject technology described herein.
Figure 3B:
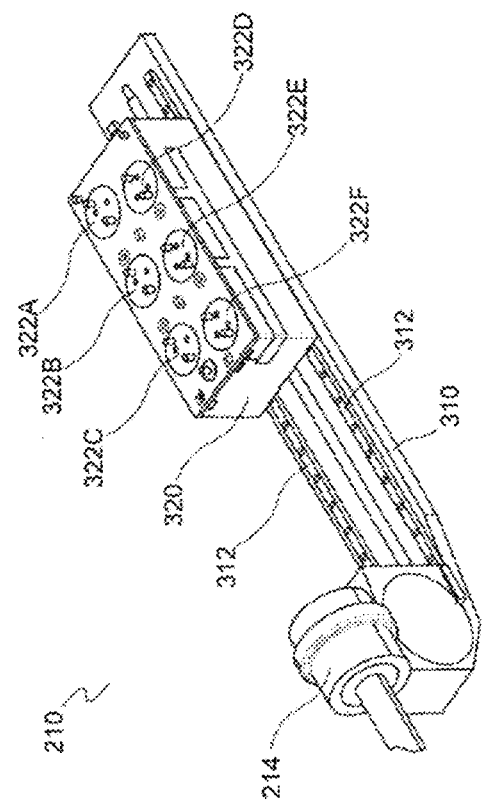

FIGS. 3A and 3B are schematic diagrams illustrating an exemplary tool drive 210 with and without a loaded tool 220, respectively, in accordance with aspects of the subject technology. As shown in FIGS. 3A and 3B, in one variation, the tool drive 210 may include an elongated base (or "stage") 310 having longitudinal tracks 312 and a tool carriage 320, which is slidingly engaged with the longitudinal tracks 312. The stage 310 may be configured to couple to the distal end of a robotic arm such that articulation of the robotic arm may position and/or orient the tool drive 210 in space. Additionally, the tool carriage 320 may be configured to receive a tool base 352 of the tool 220, which may also include a tool shaft 354 extending from the tool base 352 and through the cannula 214 of the tool drive 210, with the end effector 222 (not shown) disposed at the distal end.

Additionally, the tool carriage 320 may actuate a set of articulated movements of the end effector 222, such as through a cable system or wires manipulated and controlled by actuated drives (the terms "cable" and "wire" are used interchangeably throughout this application). The tool carriage 320 may include different configurations of actuated drives. For example, the rotary axis drives may include a motor with a hollow rotor and a planetary gear transmission at least partially disposed within the hollow rotor. The plurality of rotary axis drives may be arranged in any suitable manner. For example, the tool carriage 320 may include six rotary drives 322A-322F arranged in two rows, extending longitudinally along the base 310 that are slightly staggered to reduce width of the carriage 320 and increase the compact nature of the tool drive 210. As clearly shown in FIG. 3B, rotary drives 322A, 322B, and 322C may be generally arranged in a first row, while rotary drives 322D, 322E, and 322F may be generally arranged in a second row that is slightly longitudinally offset from the first row.

Figure 4:
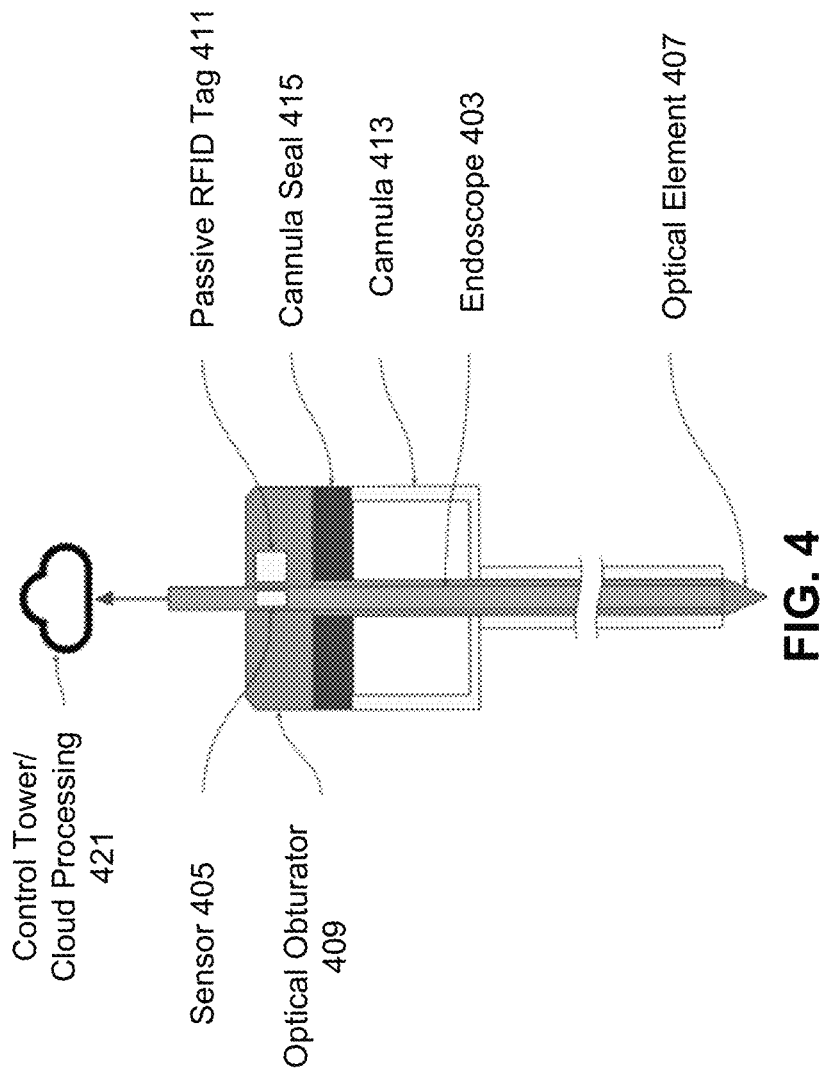
FIG. 4 shows a cross-sectional pictorial view of an exemplary endoscope with a sensor for sensing placement of the endoscope in an optical trocar, in accordance with aspects of the subject technology described herein.

FIG. 4 shows a cross-sectional pictorial view of an exemplary endoscope 403 with a sensor 405 for sensing placement of the endoscope 403 in an optical trocar, in accordance with aspects of the subject technology. Note that although systems, methods, and techniques are described for an endoscope to sense when it is placed in a trocar or cannula so as to automatically configure the endoscope for use in a surgical procedure, the subject technology may be applied to other surgical tools. Such tools may include, but are not limited to, graspers, grippers, forceps, needle drivers, retractors, and cautery instruments.

Prior to the initial insertion of the endoscope 403 into a patient for optical entry, the endoscope 403 may be assembled in an optical trocar that includes a cannula 413 sealed by a cannula seal 415 and an optical obturator 409. The endoscope 403 may be connected to the surgical robotic system, such as the control tower 3 or a cloud processing unit 421 to receive power or configuration commands. The optical obturator 409 is embedded with a passive RFID tag 411 that may be read by the sensor 405 of the endoscope 403. When the endoscope 403 is inserted into the optical obturator 409, the sensor 405 may read the passive RFID tag 411 to sense that the endoscope 403 has been inserted into the optical obturator 409. In one embodiment, the endoscope 403 may use other types of near-field communication (NFC) with passive or active tags or may use two-way communication links such as Bluetooth to sense the optical obturator 409. The sensed data may be transmitted to the control tower 3 or cloud processing unit 421 for identification of the optical obturator 409.

An optical element 407 at the distal tip of the endoscope 403 contains a camera for capturing videos of the interior of the patient. In one embodiment, the endoscope 403 may be a 3D endoscope that uses stereo images from two cameras to provide information for depth perception. The captured videos may be communicated to the control tower 3 or cloud processing unit 421 for image processing. In one embodiment, a processor may be embedded in the optical element 407 to perform some image processing function in what is referred to as a chip-on-top endoscope.

During optical entry, a surgeon may insert the optical trocar through a small incision made in the patient and may use the optical obturator 409 to puncture through successive tissue layers of the abdominal or thoracic cavity to determine the proper placement of the endoscope 403 at the surgical site. The control tower 3, cloud processing unit 421, or the processor in the endoscope 403, upon identifying the optical obturator 409 based on the sensed data from the passive RFID tag 411, may adjust configuration settings of the endoscope 403. In one embodiment, the endoscope's field of view may be modified to correct the obstructed visualization caused by the geometry of the optical obturator 409 or to otherwise optimize the visual experience during optical entry. For example, modifications to the field of view may include image cropping, zooming, color preset, image rectification, etc. To simplify operation, the same endoscope used for optical entry may be used for the laparoscope surgery throughout the robotic procedures. Thus, after optical entry, the endoscope 403 and the optical obturator 409 may be retracted from the cannula 413 while leaving the cannula 413 in place in the patient. The surgeon may dispose of the optical obturator 409 and then re-insert the endoscope 403 back into the cannula 413 until it reaches the proper surgical site again. In one embodiment, the endoscope 403 may leverage the capability of the sensor 405 to sense the type of cannula 413 into which it is inserted to automatically configure the endoscope settings for a specific procedure.

Figure 5:
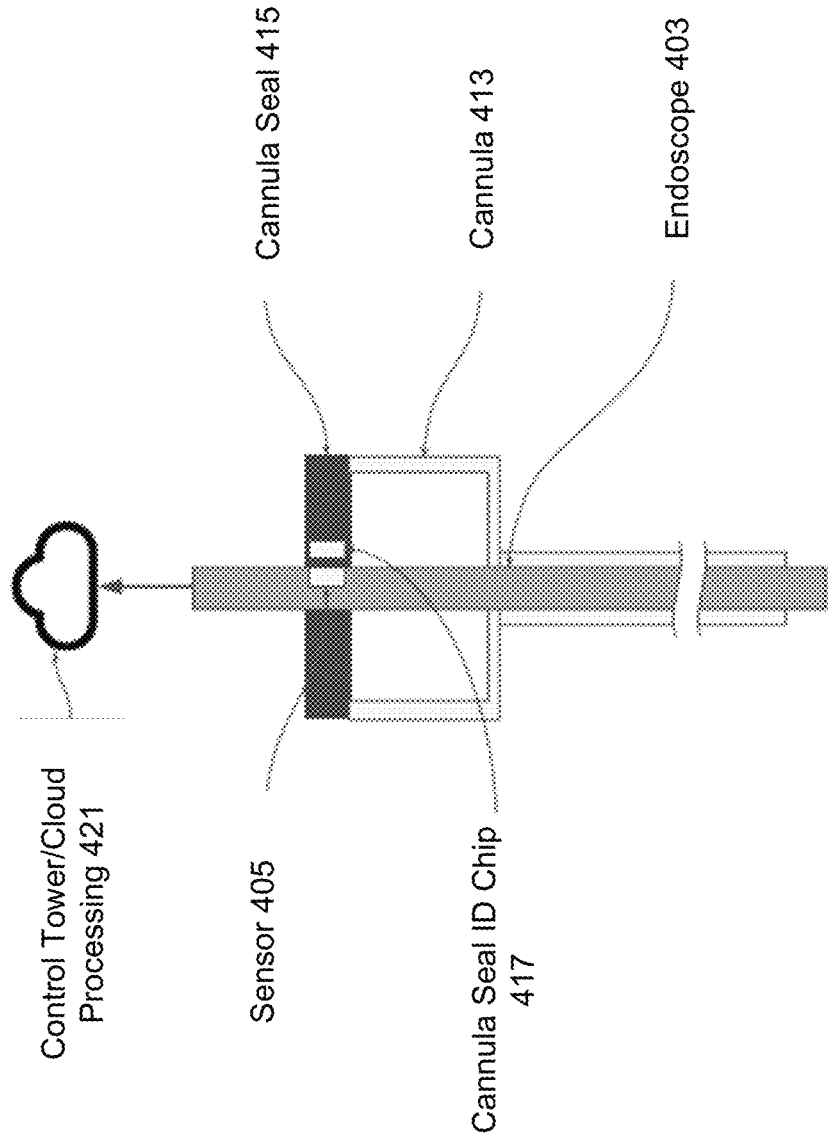
FIG. 5 shows a cross-sectional pictorial view of an exemplary endoscope with a sensor for sensing placement of the endoscope in a procedure-specific cannula, in accordance with aspects of the subject technology described herein.

FIG. 5 shows a cross-sectional pictorial view of the exemplary endoscope 403 with the sensor 405 for sensing placement of the endoscope in a procedure-specific cannula 413, in accordance with aspects of the subject technology described herein. The cannula 413 may be embedded with a passive RFID tag such as ID chip 417 that identifies the procedure-specific cannula 413. The ID chip 417 may be embedded within the cannula seal 415 that is one-time use only and may be disposed of after a surgical procedure. When the endoscope 403 is inserted into the cannula 413, the sensor 405 may read the cannula seal ID chip 417 to sense that the endoscope 403 is placed in the procedure-specific cannula 413. In one embodiment, the cannula seal ID chip 417 may be a passive or active tags used in various near-field communication (NFC) protocol or a transceiver in a Bluetooth link.

The control tower 3, cloud processing unit 421, or a processor in the endoscope 403, may receive the sensed data from the cannula seal ID chip 417 to identify the cannula 413 as specific to a surgical procedure and may adjust configuration settings of the endoscope 403 accordingly. In one embodiment, the configuration setting of the endoscope 403 may be adjusted to improve the safety and effectiveness of the endoscope 403 for the specific procedure identified, for example by adjusting color tuning, contrast, focal length, electrosurgical setting, etc. In one embodiment, when a button on the endoscope 403 is pushed, a robotic arm attached to the endoscope 403 may be driven to an initial pose of the identified procedure. In one embodiment, the endoscope 403 may sense when it is outside of, or retracted from, the cannula 413 so as to automatically switch to a configuration setting associated with a non-operational mode.

Figure 6:
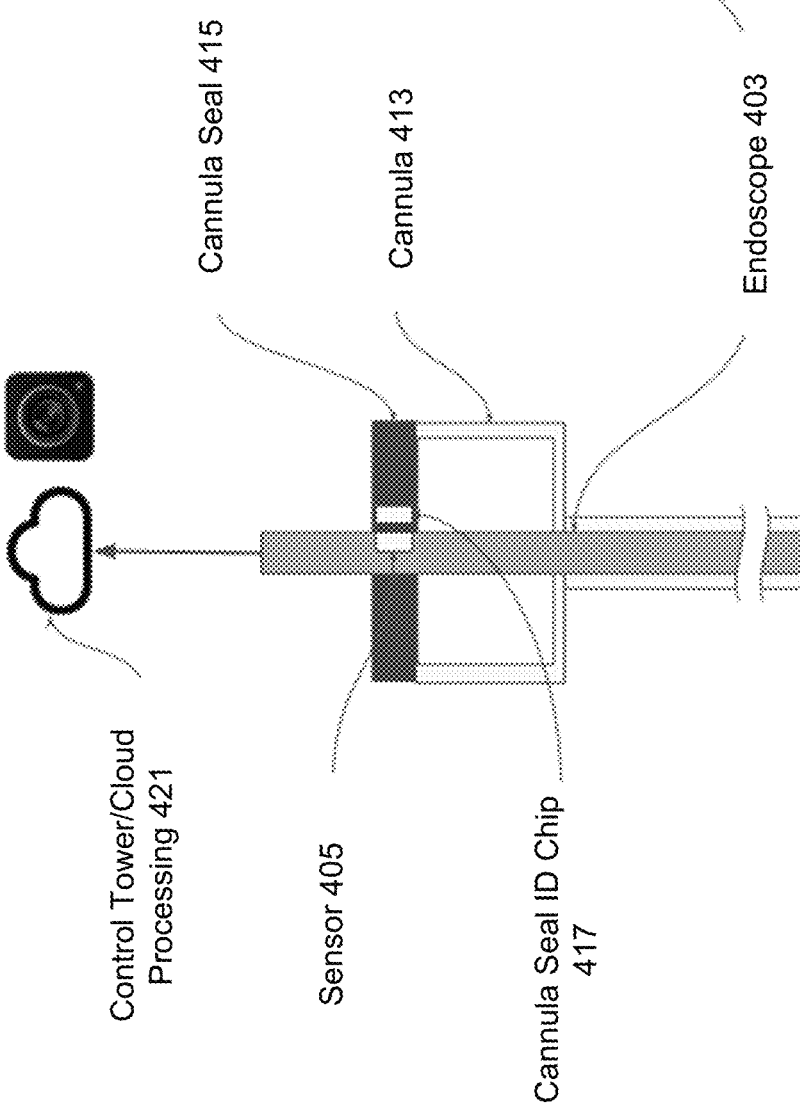
FIG. 6 shows a cross-sectional pictorial view of an exemplary endoscope with a sensor for sensing placement of the endoscope in a cannula to enable automatic segmentation of video recorded by the endoscope when the endoscope is outside of the cannula, in accordance with aspects of the subject technology described herein.

FIG. 6 shows a cross-sectional pictorial view of the exemplary endoscope 403 with the sensor 405 for sensing placement of the endoscope in the cannula 413 to enable automatic segmentation of video recorded by the endoscope 403 when the endoscope 403 is outside of the cannula 413, in accordance with aspects of the subject technology described herein. The sensor 405 may detect the directional movement of the endoscope 403 as the sensor 405 slides past the cannula seal ID chip 417.

In one embodiment, there may be two sensors embedded in the endoscope 403. The two sensors are spaced apart along the longitudinal axis of the endoscope 403. When the surgeon inserts the endoscope 403 into the cannula 413, the sensor closer to the distal tip of the endoscope 403 may read the cannula seal ID chip 417 first before the second sensor. The control tower 3, cloud processing unit 421, or a processor in the endoscope 403 may interpret such order of ID sensing by the sensors as indicating an insertion of the endoscope 403 into the patient's body. Display or recording of the captured videos by the control tower 3 may then be automatically enabled.

Conversely, when the surgeon retracts the endoscope 403 from the cannula 413, the sensor further from the distal tip of the endoscope 403 may read the cannula seal ID chip 417 first before the other sensor. The control tower 3, cloud processing unit 421, or the processor in the endoscope 403 may interpret such order of ID sensing by the sensors as indicating removal of the endoscope 403 from the patient's body. The control tower 3 may then automatically turn off video capture or recording, or a video recording system may automatically segment the videos to remove the portion captured when the endoscope 403 is external to the patient. Doing so may eliminate inadvertent recording of personal health information of the patient to ensure compliance with the patient's privacy rights when the endoscope 403 is outside of the patient's body.

Figure 7:
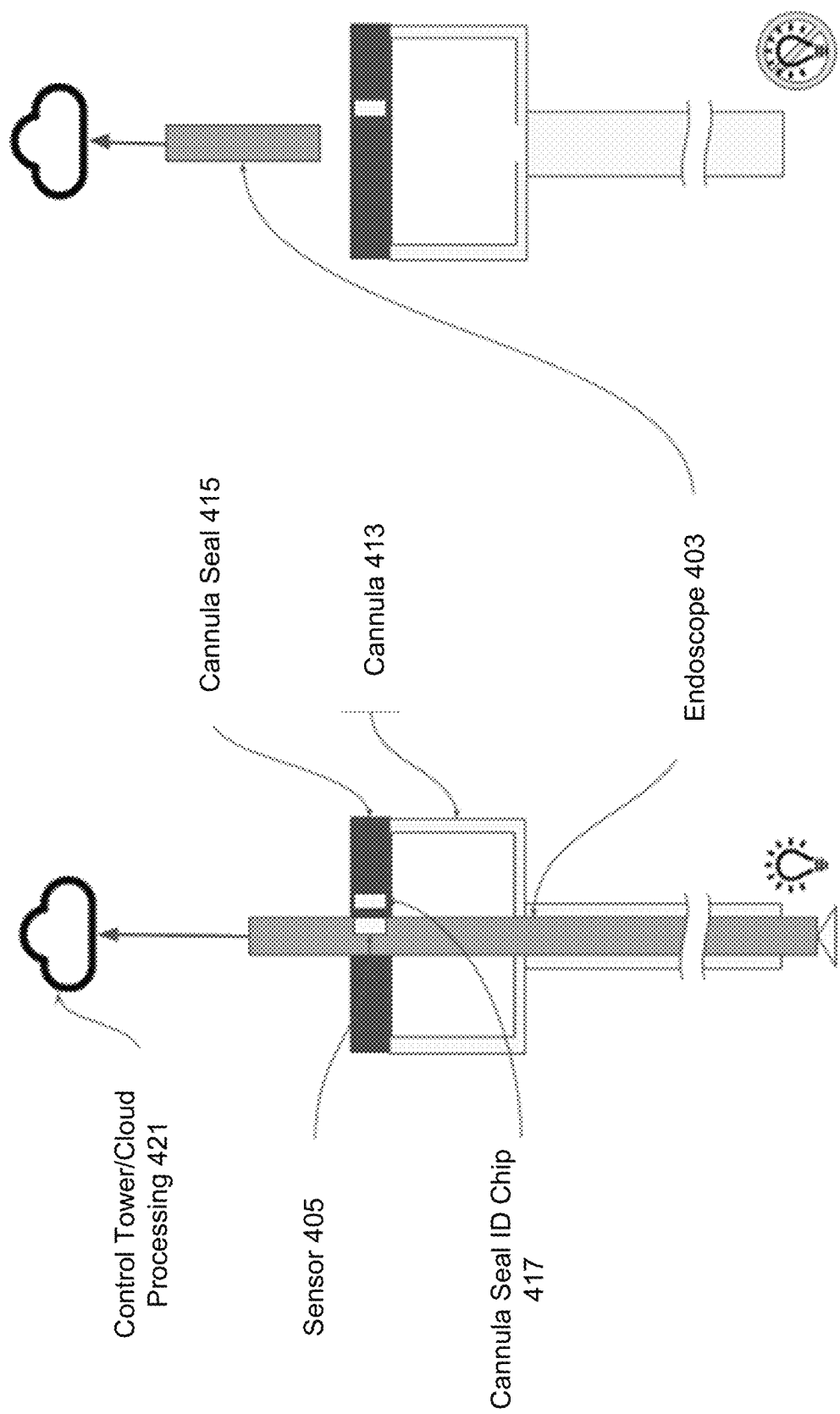
FIG. 7 shows a cross-sectional pictorial view of an exemplary endoscope with a sensor for sensing placement of the endoscope in a cannula to enable automatic shutoff of the endoscope light when the endoscope is outside of the cannula, in accordance with aspects of the subject technology described herein.

FIG. 7 shows a cross-sectional pictorial view of the exemplary endoscope 403 with the sensor 405 for sensing placement of the endoscope 403 in a cannula 413 to enable automatic shutoff of the endoscope light when the endoscope 403 is outside of the cannula 413, in accordance with aspects of the subject technology described herein. By sensing the whether the endoscope 403 is outside or inside the patient's body, the endoscope 403 may automatically switch between functional and non-functional modes.

For example, when the sensed data from the sensor 405 indicates that the endoscope 403 is being inserted into the patient's body through the cannula 413, the control tower 3, cloud processing unit 421, or a processor in the endoscope 403 may automatically turn on the light source of the endoscope 403. Conversely, when the sensed data from the sensor 405 indicates that the endoscope 403 is being removed from the patient's body or is outside of the patient's body, the control tower 3, cloud processing unit 421, or the processor in the endoscope 403 may automatically turn off the light source of the endoscope 403. Doing so may prevent patient burns, blinding of bedside assistants, or operating room fires when the tip or the optical element 407 of the endoscope 403 is in contact with a surgical drape or patient skin. In one embodiment, automatic sensing of the operating environment by the endoscope 405 may extend to sensing by the endoscope 405 of a surgical instrument or accessory used in conjunction with the endoscope 405 or the operating condition of the surgical instrument or accessory.

Figure 8:
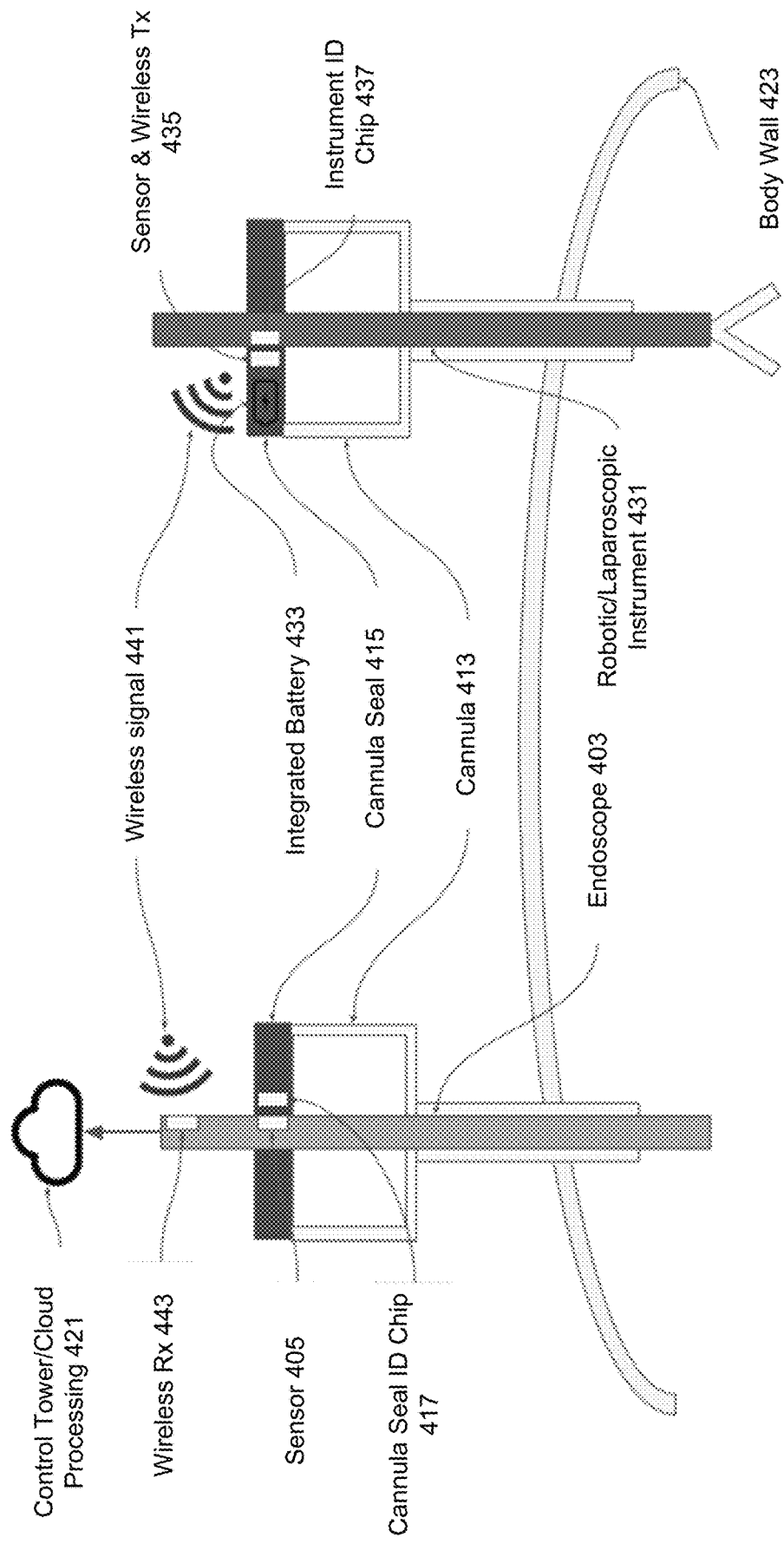
FIG. 8 shows a cross-sectional pictorial view of an exemplary endoscope with a sensor for sensing placement of the endoscope in a cannula and a wireless receiver for receiving information from a laparoscopic instrument in another cannula, in accordance with aspects of the subject technology described herein.

FIG. 8 shows a cross-sectional pictorial view of the exemplary endoscope 403 with the sensor 405 for sensing placement of the endoscope 403 in a cannula 413 and a wireless receiver 443 for receiving information from a robotic or laparoscopic instrument 431 in another cannula 413, in accordance with aspects of the subject technology described herein. The endoscope 403 and the robotic or laparoscopic instrument 431 may form a mesh network for the endoscope 403 to receive operational information or environmental condition from the robotic or laparoscopic instrument 431 used in conjunction with the endoscope 403.

The endoscope 403 again has a sensor 405 for reading the cannula seal ID chip 417 to sense that the endoscope 403 is placed in a procedure-specific cannula 413. In addition, the endoscope 403 may use the wireless receiver 443 to receive information from the robotic or laparoscopic instrument 431. In one embodiment, the wireless receiver 443 may operate using one of a variety of short-range wireless links such as Bluetooth. In one embodiment, the robotic or laparoscopic instrument 431 may include an instrument ID chip 437 that identifies the robotic or laparoscopic instrument 431. The cannula 413 into which the robotic or laparoscopic instrument 431 is inserted may have a sensor and wireless transmitter 435 with an integrated battery 433 embedded in the cannula seal 415. When the robotic or laparoscopic instrument 431 is inserted through the cannula 413 into the body wall 423 of the patient, the sensor and wireless transmitter 435 of the cannula 413 may read the instrument ID chip 437 to detect the robotic or laparoscopic instrument 431. The sensor and wireless transmitter 435 may transmit information such as identification or operational information of the robotic or laparoscopic instrument 431 to the endoscope 403 through wireless signal 441 using one of a variety of short-range wireless protocols such as Bluetooth. In one embodiment, the robotic or laparoscopic instrument 431 may have a sensor and wireless transmitter, and the cannula 413 may be embedded with a procedure-specific ID in the cannula seal 415. When the robotic or laparoscopic instrument 431 is inserted into the cannula 413, the sensor and wireless transmitter of the robotic or laparoscopic instrument 431 may read the procedure-specific ID to transmit information about the procedure and the instrument 431 to the endoscope 403.

The endoscope 403 may transmit the information about the robotic or laparoscopic instrument 431 as well as the information about the endoscope 403 to the control tower 3 or the cloud processing unit 421 for the surgical robotic system to adapt to the surgical environment. The endoscope 403 may receive feedback information from the control tower 3 or the cloud processing unit 421 to adjust the configuration setting of the endoscope 403. For example, when the robotic or laparoscopic instrument 431 is a cautery instrument that may generate smoke when cauterizing tissues (e.g., a monopolar pencil that is currently firing), the visualization setting of the endoscope 403 may be changed to see through the smoke.

Figure 9:
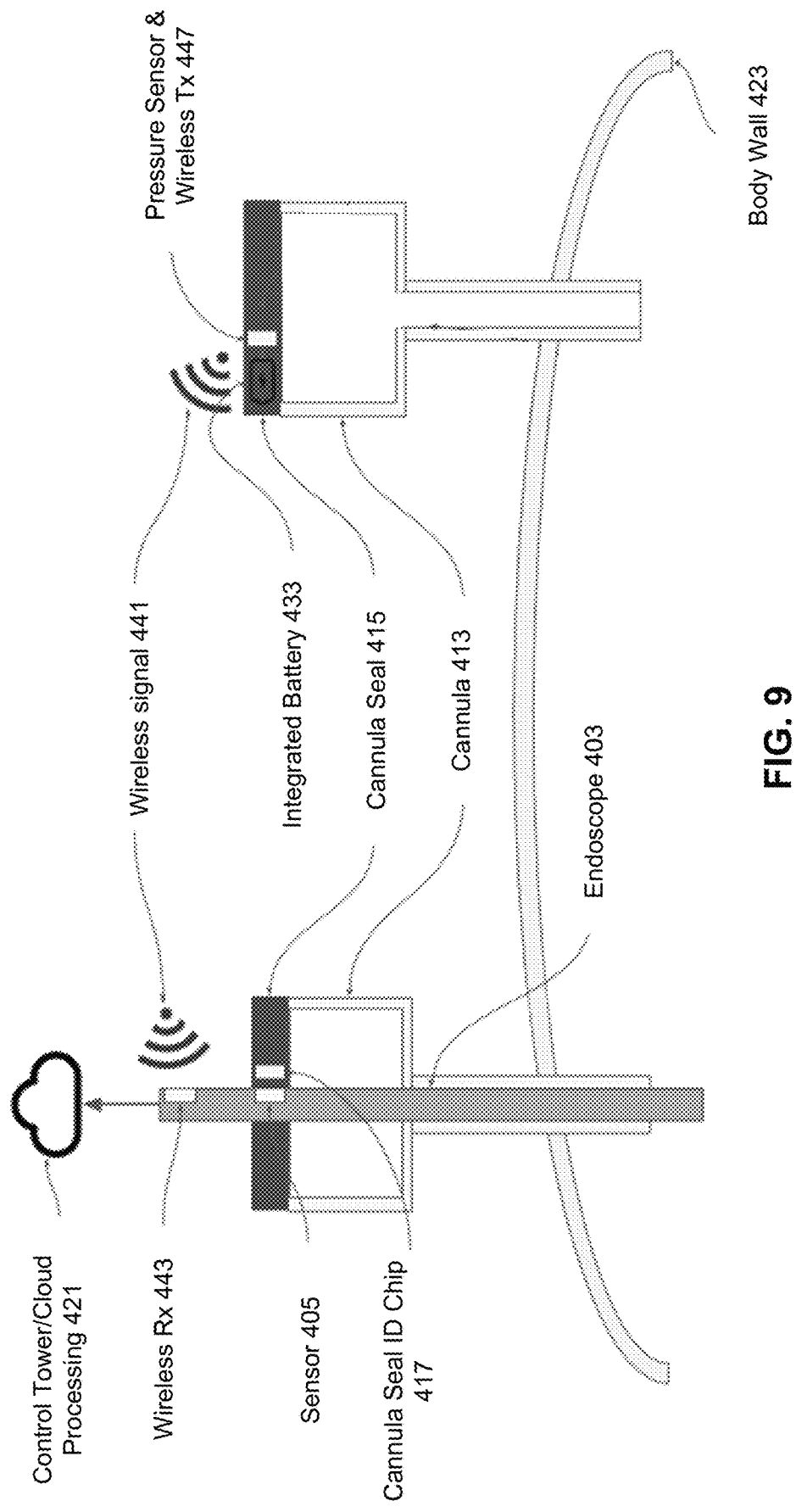
FIG. 9 shows a cross-sectional pictorial view of an exemplary endoscope with a sensor for sensing placement of the endoscope in a cannula and a wireless receiver for receiving pressure data of the patient sensed by another cannula, in accordance with aspects of the subject technology described herein.

FIG. 9 shows a cross-sectional pictorial view of an exemplary endoscope 403 with a sensor 405 for sensing placement of the endoscope 403 in a cannula 413 and a wireless receiver 443 for receiving pressure data of the patient sensed by a second cannula, in accordance with aspects of the subject technology described herein. The second cannula has a pressure sensor and wireless transmitter 447 with an integrated battery 433 embedded in the cannula seal 415 to sense the insufflation pressure in the body cavity of the patient. The pressure sensor and wireless transmitter 447 may transmit the sensed insufflation pressure to the endoscope 403 through wireless signal 441.

The endoscope 403 may transmit the live reporting of the insufflation pressure as well as the information about the endoscope 403 to the control tower 3 or the cloud processing unit 421 for the surgical robotic system to adapt to the surgical environment. The surgeons or the staff may monitor the insufflation pressure through the surgical procedure to take corrective measures when the insulation pressure becomes excessive. In one embodiment, the endoscope 403 may receive feedback information from the control tower 3 or the cloud processing unit 421 to modify the operation of the second cannula or to adjust the configuration settings of a laparoscopic instrument in the second cannula. The endoscope 403 may relay the feedback information to the second cannula or the laparoscopic instrument.

Figure 10:
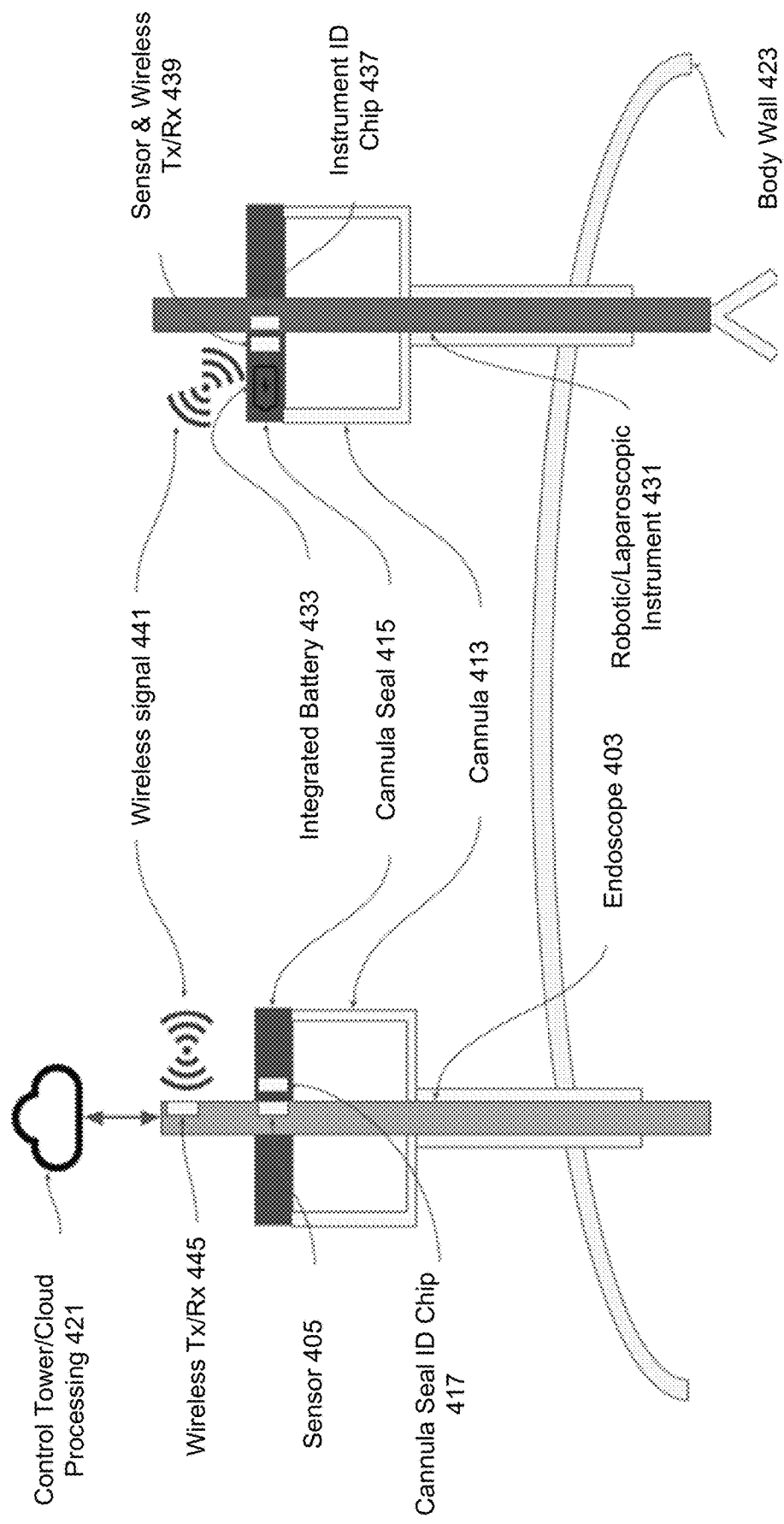
FIG. 10 shows a cross-sectional pictorial view of an exemplary endoscope with a sensor for sensing placement of the endoscope in a cannula and a wireless transceiver for two-way communication with a laparoscopic instrument sensed by another cannula, in accordance with aspects of the subject technology described herein.

FIG. 10 shows a cross-sectional pictorial view of an exemplary endoscope 403 with a sensor 405 for sensing placement of the endoscope 403 in a cannula 413 and a wireless transceiver 445 for two-way communication with a laparoscopic instrument 431 sensed by a second cannula, in accordance with aspects of the subject technology described herein. In contrast to the one-way communication of FIG. 8, the endoscope 403 may carry on two-way communication with the second cannula to relay feedback information to the second cannula or the laparoscopic instrument 431.

The laparoscopic instrument 431 has a sensor and wireless transceiver 439 with an integrated battery 433 embedded in the cannula seal 415. The sensor and wireless transceiver 439 allows the second cannula to transmit identification or operational information of the laparoscopic instrument 431 to the wireless transceiver 445 of the endoscope 403 and to also receive adjusted configuration settings of the laparoscopic instrument 431 from the endoscope 403. In one embodiment, the adjusted configuration settings may be received by the endoscope 403 from the control tower 3 or the cloud processing unit 421. In one embodiment, the endoscope 403 may generate the adjusted configuration settings for the laparoscopic instrument 431 based on feedback information such as visual feedback of processed images, information on the surgical procedure, sensed data of other sensors or cannulas, etc., received from the control tower 3 or the cloud processing unit 421. The adjusted configuration settings may improve the operation of the laparoscopic instrument 431 when used in conjunction with the endoscope 403. For example, when the laparoscopic instrument 431 is a cautery instrument, the firing energy of the cautery instrument may be adjusted to work with the visualization setting of the endoscope 403 to allow the endoscope 403 to see through the smoke.

Figure 11:
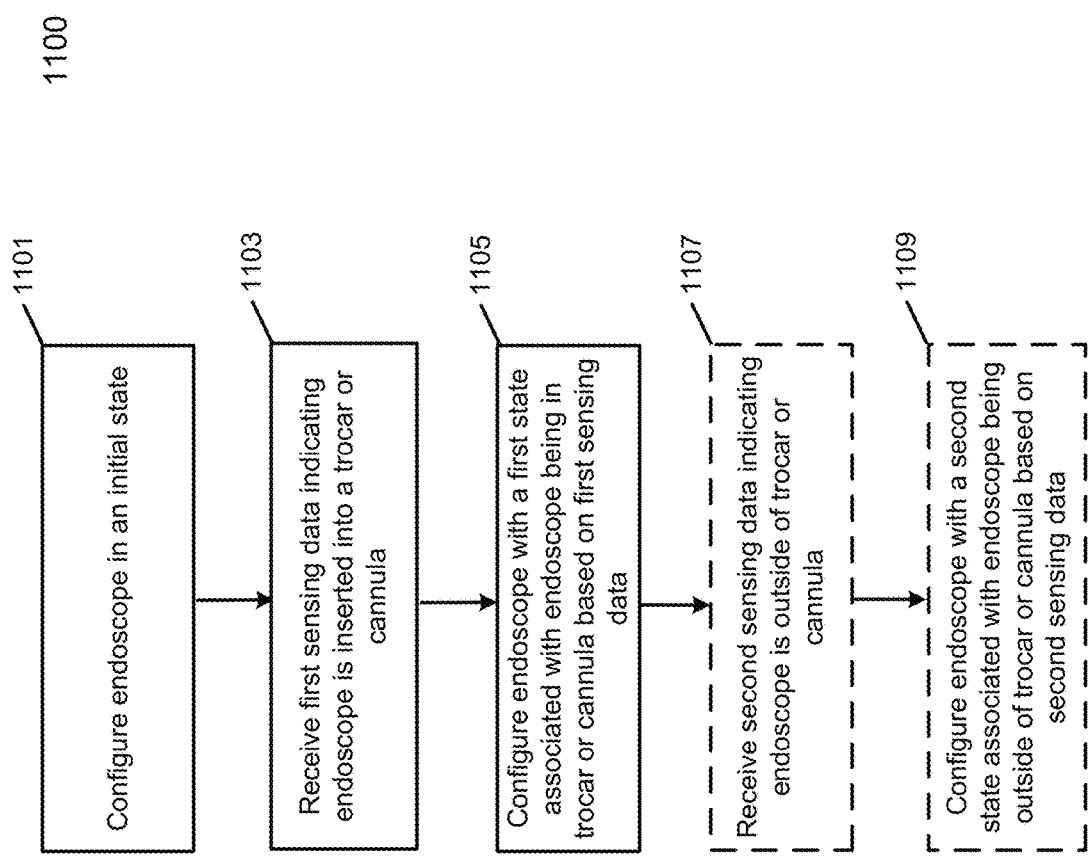
FIG. 11 is a flow chart illustrating a method for a control system to process environmental information sensed by an endoscope and to configure the endoscope in response to the sensed information, in accordance with aspects of the subject technology described herein.

FIG. 11 is a flow chart illustrating a method 1100 for a control system to process environmental information sensed by an endoscope and to configure the endoscope in response to the sensed information, in accordance with aspects of the subject technology described herein. The method 1100 may be implemented by the control tower 3 of FIG. 1, the control tower or cloud processing unit 421 of FIGS. 4-10, or the endoscope itself.

At block 1101, the control system configures the endoscope in an initial state. For example, prior to the initial insertion of the endoscope into a patient for optical entry, the endoscope may be configured with a default field of view.

At block 1103, the control system receives first sensing data from the endoscope indicating that the endoscope is inserted into a trocar or cannula. In one embodiment, an embedded sensor of the endoscope may read an RFID tag embedded into an optical obturator of a trocar to sense that the endoscope has been inserted into the trocar for optical entry into a patient. In one embodiment, the sensor of the endoscope may read an RFID tag embedded into a procedure-specific cannula to sense that the endoscope has been inserted into the procedure-specific cannula. The sensor may send the first sensing data to the control system.

At block 1105, based on the first sensing data, the control system configures the endoscope with a first state associated with the endoscope being in the trocar or the cannula. In one embodiment, based on the first sensing data indicating that the endoscope has been inserted into a trocar for optical entry, the control system may adjust the field of view of the endoscope by configuring the endoscope to perform image cropping, zooming, color preset, image rectification, etc., so as to correct the obstructed visualization caused by the geometry of the optical obturator during optical entry. In one embodiment, based on the first sensing data indicating that the endoscope has been inserted into a procedure-specific cannula, the control system may adjust the color tuning, contrast, focal length, electrosurgical setting, etc., of the endoscope to improve the safety and effectiveness of the endoscope for the specific procedure identified. In one embodiment, the control system may turn on the light source of the endoscope or may enable the display or the recording of the videos captured by the endoscope when the first sensing data indicates the endoscope is inserted into a cannula.

At block 1107, the control system receives second sensing data from the endoscope indicating that the endoscope is outside of the trocar or cannula. The control system may not receive the second sensing signal if the endoscope remains inserted in the trocar or cannula. In one embodiment, the embedded sensor of the endoscope may sense the directional movement of the endoscope as the sensor slides past the RFID tag. For example, when the sensor reads again the RFID tag of the trocar or cannula while the endoscope is in a state associated with being in the trocar or cannula, the sensor may sense that the endoscope is being retracted or removed from the trocar or cannula. In one embodiment, the endoscope may have two embedded sensors spaced apart along the longitudinal axis of the endoscope for the endoscope to sense the directional movement of the endoscope. The sensor may send the second sensing data to the control system.

At block 1109, based on the second sensing data, the control system configures the endoscope with a second state associated with the endoscope being outside of the trocar or the cannula. In one embodiment, the control system may turn off the light source of the endoscope or may turn off the videos captured by the endoscope when the second sensing data indicates the endoscope is outside of the trocar or the cannula. In one embodiment, control system may automatically segment the videos to remove the portion of the videos captured when the endoscope is outside of the trocar or the cannula and thus external to the patient. In one embodiment, the second state associated with the endoscope being outside of the trocar or the cannula may be the initial state of block 1101.

Figure 12:
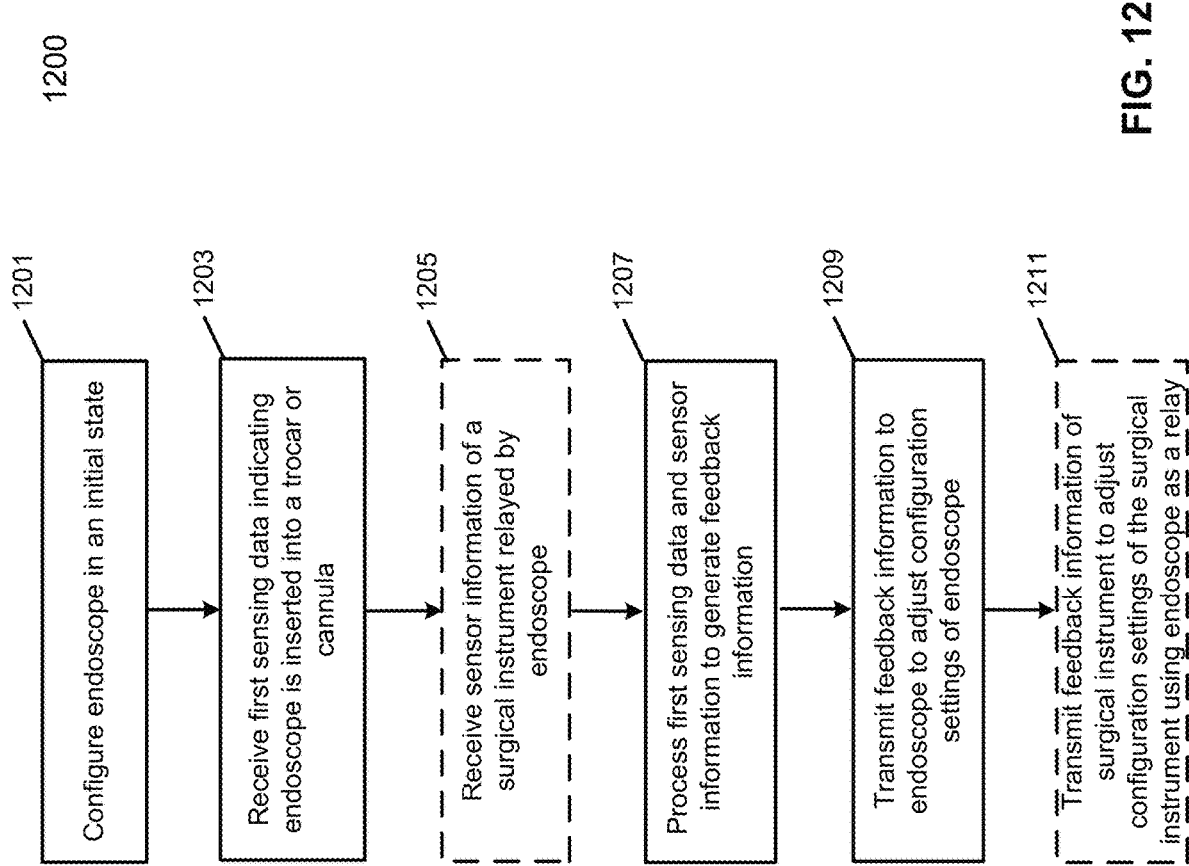
FIG. 12 is a flow chart illustrating a method for a control system to process information sensed by an endoscope and information relayed by the endoscope but sensed by another laparoscopic instrument for the control system to configure the endoscope and the laparoscopic instrument, in accordance with aspects of the subject technology described herein.

FIG. 12 is a flow chart illustrating a method 1200 for a control system to process information sensed by an endoscope and information relayed by the endoscope but sensed by another laparoscopic instrument for the control system to configure the endoscope and the laparoscopic instrument, in accordance with aspects of the subject technology described herein. The method 1200 may be implemented by the control tower 3 of FIG. 1, the control tower or cloud processing unit 421 of FIGS. 4-10, or the endoscope itself.

Blocks 1201 and 1203 may be the same as blocks 1101 and 1103 and will not be repeated for brevity. At block 1205, the control system receives sensor information of a laparoscopic instrument relayed by the endoscope. If the endoscope does not receive or is incapable of receiving sensor information of a laparoscopic instrument, the method 1200 may skip blocks 1205 and 1211. The endoscope may receive the sensor information of the laparoscopic instrument from another cannula that senses that the laparoscopic instrument is inserted through it. The sensor information may contain identification or operational information of the laparoscopic instrument. In one embodiment, the sensor information may be data sensed by the other cannula such as insufflation pressure of the patient. The endoscope may act as a relay to transmit the sensor information to the control system.

At block 1207, the control system processes the first sensing data of the endoscope and the sensor information of the laparoscopic instrument to generate feedback information to adapt the endoscope and the laparoscopic instrument to the surgical environment. For example, when the laparoscopic instrument is a cautery instrument, the control system may change the visualization setting of the endoscope while adjusting the firing energy of the cautery instrument to improve their operations. In one embodiment, if the control system does not receive sensor information of a laparoscopic instrument relayed by the endoscope, or if the endoscope is incapable of transmitting to the laparoscopic instrument, the control system may process the first sensing data of the endoscope to generate feedback information for the endoscope only.

At block 1209, the control system transmits the feedback information to the endoscope to adjust the configuration settings of the endoscope. In one embodiment, based on the first sensing data indicating that the endoscope has been inserted into a procedure-specific cannula, the control system may adjust the color tuning, contrast, focal length, electrosurgical setting, etc., of the endoscope to improve the safety and effectiveness of the endoscope for the specific procedure identified. In one embodiment, when the control system receives sensor information of a cautery instrument, the feedback information may change the visualization setting of the endoscope to see through the smoke that may be generated when a cautery instrument is used to cauterize tissues.

At block 1211, if there is feedback information for the laparoscopic instrument, the control system transmits the feedback information to adjust the configuration settings of the laparoscopic instrument to the endoscope for the endoscope to relay the feedback information to the laparoscopic instrument. For example, if the laparoscopic instrument is a cautery instrument, the feedback information may adjust the firing energy of the cautery instrument.

Figure 13:
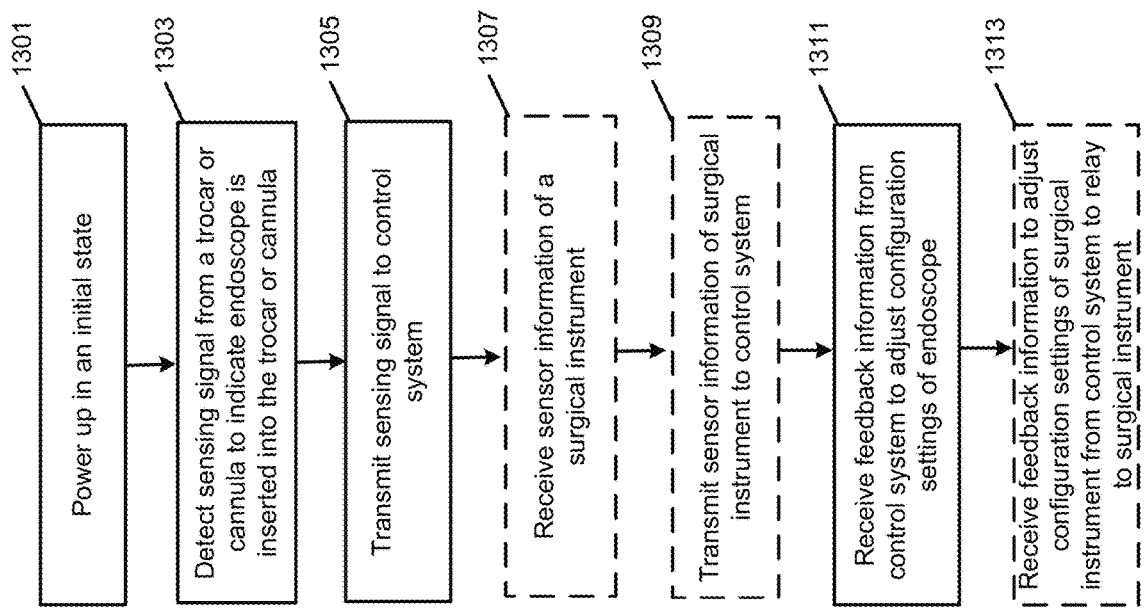
FIG. 13 is a flow chart illustrating a method 1300 for an endoscope to transmit information sensed by the endoscope to a control system and for the endoscope to receive feedback information from the control system to adjust configuration settings of the endoscope, in accordance with aspects of the subject technology described herein.

FIG. 13 is a flow chart illustrating a method 1300 for an endoscope to transmit information sensed by the endoscope to a control system and for the endoscope to receive feedback information from the control system to adjust configuration settings of the endoscope, in accordance with aspects of the subject technology described herein. In one embodiment, if the endoscope receives information sensed by a laparoscopic instrument, the endoscope may transmit the sensed information from the laparoscopic instrument to the control system. The endoscope may receive feedback information for the laparoscopic instrument from the control system and may relay the feedback information to the laparoscopic instrument to adjust configuration settings of the laparoscopic instrument.

At block 1301, the endoscope powers up in an initial state. For example, prior to the initial insertion of the endoscope into a patient for optical entry, the endoscope may be configured with a default field of view.

At block 1303, the endoscope detects sensing signal from a trocar or cannula indicating that the endoscope is inserted into the trocar or cannula. In one embodiment, an embedded sensor of the endoscope may read an RFID tag embedded into an optical obturator of a trocar to sense that the endoscope has been inserted into the trocar for optical entry into a patient. In one embodiment, the sensor of the endoscope may read an RFID tag embedded into a procedure-specific cannula to sense that the endoscope has been inserted into the procedure-specific cannula.

At block 1305, the endoscope transmits the sensing signal to the control system for processing.

At block 1307, the endoscope receives sensor information of a laparoscopic instrument.

If the endoscope does not receive or is incapable of receiving sensor information of a laparoscopic instrument, the method 1300 may skip blocks 1307, 1309, and 1313. In one embodiment, the endoscope may have a wireless receiver such as a Bluetooth receiver to receive the sensor information of the laparoscopic instrument transmitted from another cannula that senses that the laparoscopic instrument is inserted through it. The sensor information may contain identification or operational information of the laparoscopic instrument. In one embodiment, the sensor information may be data sensed by the other cannula such as insufflation pressure of the patient.

At block 1309, the endoscope acts as a relay to transmit the sensor information of the laparoscopic instrument to the control system for processing.

At block 1311, the endoscope receives feedback information from the control system to adjust the configuration settings of the endoscope. In one embodiment, based on the sensing data indicating that the endoscope has been inserted into a trocar for optical entry, the feedback information from the control system may configure the endoscope to perform image cropping, zooming, color preset, image rectification, etc., so as to correct the obstructed field of view caused by the geometry of the optical obturator during optical entry. In one embodiment, the feedback information may turn on the light source of the endoscope or may enable the display or the recording of the videos captured by the endoscope when the sensing data indicates the endoscope is inserted into a cannula.

At block 1313, the endoscope receives feedback information from the control system to adjust the configuration settings of the laparoscopic instrument. The endoscope may relay the feedback information to the laparoscopic instrument. For example, if the laparoscopic instrument is a cautery instrument, the feedback information may be used to adjust the firing energy of the cautery instrument. If the endoscope is incapable of transmitting to the laparoscopic instrument, the endoscope may transmit information on its capability to the control system so that the endoscope does not receive feedback information for the laparoscopic instrument.

Figure 14:
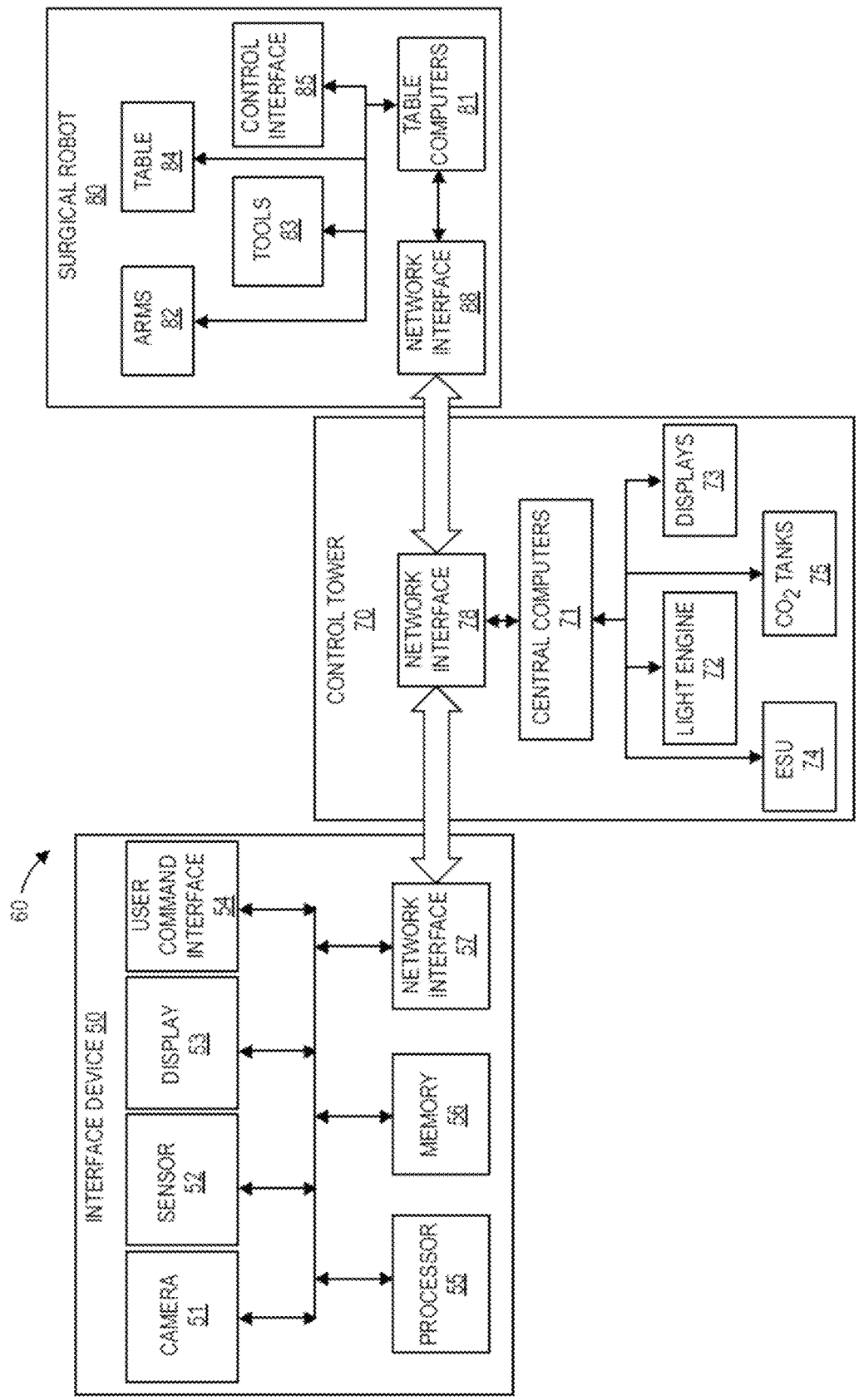
FIG. 14 is a block diagram illustrating exemplary hardware components of a surgical robotic system, in accordance with aspects of the subject technology described herein.

FIG. 14 is a block diagram illustrating exemplary hardware components of a surgical robotic system, in accordance with aspects of the subject technology. The surgical robotic system may include an interface device 50, a surgical robot 80, and a control tower 70. The surgical robotic system may include other or additional hardware components; thus, the diagram is provided by way of example and not a limitation to the system architecture.

The interface device 50 includes a camera 51, sensor 52, display 53, user command interface 54, processor 55, memory 56, and network interface 57. The camera 51 and the sensor 52 may be configured to capture color images and depth-image information of the surgical robotic system such as those captured by an endoscope. Images captured by the camera 51 and sensor 52 may be projected on the display 53. The processor 55 may be configured to run an operating system to control the operation of the interface device 50. The memory 56 may store the image processing algorithms, operating system, program codes, and other data memories used by the processor 55.

The user command interface 54 may include the interface for other features such as the Web portal. The hardware components may communicate via a bus. The interface device may use the network interface 57 to communicate with the surgical robotic system through an external interface. The external interface may be a wireless or a wired interface.

The control tower 70 may be a mobile point-of-care cart housing touchscreen displays, computers that control the surgeon's robotically-assisted manipulation of instruments, safety systems, graphical user interface (GUI), light source, and video and graphics computers. The control tower 70 may comprise central computers 71 that may include at least a visualization computer, a control computer, and an auxiliary computer, various displays 73 that may include a team display and a nurse display, and a network interface 78 coupling the control tower 70 to both the interface device 50 and the surgical robot 80. The control tower 70 may also house third-party devices, such as an advanced light engine 72, an electrosurgical generator unit (ESU) 74, and insufflator and CO2 tanks 75. The control tower 70 may offer additional features for user convenience, such as the nurse display touchscreen, soft power and E-hold buttons, user-facing USB for video and still images, and electronic caster control interface. The auxiliary computer may also run a real-time Linux, providing logging/monitoring and interacting with cloud-based web services. The central computers 71 of the control tower 70 may receive the sensing data from the endoscope to implement the methods described herein for configuring the endoscope or a laparoscopic instrument.

The surgical robot 80 comprises an articulated operating table 84 with a plurality of integrated arms 82 that may be positioned over the target patient anatomy. A suite of compatible tools 83 may be attached to or detached from the distal ends of the arms 82, enabling the surgeon to perform various surgical procedures. The surgical robot 80 may also comprise control interface 85 for manual control of the arms 82, operating table 84, and tools 83. The control interface 85 may include items such as, but not limited to, remote controls, buttons, panels, and touchscreens. Other accessories such as trocars (sleeves, seal cartridge, and obturators) and drapes may also be manipulated to perform procedures with the system. In one embodiment, the plurality of the arms 82 may include four arms mounted on both sides of the operating table 84, with two arms on each side. For certain surgical procedures, an arm mounted on one side of the operating table 84 may be positioned on the other side of the operating table 84 by stretching out and crossing over under the operating table 84 and arms mounted on the other side, resulting in a total of three arms positioned on the same side of the operating table 84. The surgical tool may also comprise table computers 81 and a network interface 88, which may place the surgical robot 80 in communication with the control tower 70.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications. They thereby enable others skilled in the art to best utilize the invention and various embodiments with various modifications as are suited to the particular use contemplated. It is intended that the following claims and their equivalents define the scope of the invention.

The methods, devices, processing, and logic described above may be implemented in many different ways and in many different combinations of hardware and software. The controllers and estimators may comprise electronic circuitry. For example, all or parts of the implementations may be circuitry that includes an instruction processor, such as a Central Processing Unit (CPU), microcontroller, or a microprocessor; an Application Specific Integrated Circuit (ASIC), Programmable Logic Device (PLD), or Field Programmable Gate Array (FPGA); or circuitry that includes discrete logic or other circuit components, including analog circuit components, digital circuit components or both; or any combination thereof. The circuitry may include discrete interconnected hardware components and/or may be combined on a single integrated circuit die, distributed among multiple integrated circuit dies, or implemented in a Multiple Chip Module (MCM) of multiple integrated circuit dies in a common package, as examples.

The circuitry may further include or access instructions for execution by the circuitry. The instructions may be stored in a tangible storage medium that is other than a transitory signal, such as a flash memory, a Random Access Memory (RAM), a Read Only Memory (ROM), an Erasable Programmable Read Only Memory (EPROM); or on a magnetic or optical disc, such as a Compact Disc Read Only Memory (CDROM), Hard Disk Drive (HDD), or other magnetic or optical disk; or in or on another machine-readable medium. A product, such as a computer program product, may include a storage medium and instructions stored in or on the medium, and the instructions when executed by the circuitry in a device may cause the device to implement any of the processing described above or illustrated in the drawings.

The implementations may be distributed as circuitry among multiple system components, such as among multiple processors and memories, optionally including multiple distributed processing systems. Parameters, databases, and other data structures may be separately stored and managed, may be incorporated into a single memory or database, may be logically and physically organized in many different ways, and may be implemented in many different ways, including as data structures such as linked lists, hash tables, arrays, records, objects, or implicit storage mechanisms. Programs may be parts (e.g., subroutines) of a single program, separate programs, distributed across several memories and processors, or implemented in many different ways, such as in a library, such as a shared library (e.g., a Dynamic Link Library (DLL)). The DLL, for example, may store instructions that perform any of the processing described above or illustrated in the drawings, when executed by the circuitry.

Also, the various controllers discussed herein can take the form of processing circuitry, a microprocessor or processor, and a computer-readable medium that stores computer-readable program code (e.g., firmware) executable by the (micro)processor, logic gates, switches, an application specific integrated circuit (ASIC), a programmable logic controller, and an embedded microcontroller, for example. The controller can be configured with hardware and/or firmware to perform the various functions described below and shown in the flow diagrams. Also, some of the components shown as being internal to the controller can also be stored external to the controller, and other components can be used.

The invention claimed is:

1. A method performed by at least one processor of a surgical robotic system, comprising:
    configuring, by the at least one processor, a first surgical instrument of the surgical robotic system such that the first surgical instrument operates in an initial state while the first surgical instrument is outside of and prior to being inserted into a first cannula of a trocar;
    receiving, by the at least one processor, first sensing information from the first surgical instrument indicating that the first surgical instrument has been inserted into the first cannula;

receiving, by the at least one processor, second sensing information of a second surgical instrument or a second cannula; and responsive to receiving the first and second sensing information:

generating, by the at least one processor, first configuration information of the first surgical instrument based on the first and second sensing information, the first configuration information being used to configure the first surgical instrument to operate in a first state corresponding to when the first surgical instrument is in the first cannula; and configuring, by the at least one processor, the first surgical instrument using the first configuration information such that the first surgical instrument operates in the first state different from the initial state, wherein the first configuration information is used to configure the first surgical instrument to operate in the first state in which the first surgical instrument is operable with the second surgical instrument or the second cannula.

2. The method of claim 1, wherein receiving the first sensing information from the first surgical instrument comprises:

receiving a sensing signal from a sensor of the first surgical instrument in response to the sensor sensing a tag embedded in the first cannula when the sensor slides past the tag as the first surgical instrument is inserted into the first cannula.

3. The method of claim 2, wherein generating the first configuration information comprises:

determining that the first surgical instrument transitions from the initial state associated with the first surgical instrument being outside of the first cannula to the first state based on the sensing signal.

4. The method of claim 1, further comprising:

receiving third sensing information from the first surgical instrument indicating that the first surgical instrument is removed from the first cannula;

generating second configuration information of the first surgical instrument based on the third sensing information, the second configuration information being used to configure the first surgical instrument to operate in a second state corresponding to when the first surgical instrument is outside of the first cannula; and transmitting the second configuration information to the first surgical instrument to configure the first surgical instrument to operate in the second state.

5. The method of claim 4, wherein receiving the third sensing information from the first surgical instrument comprises:

receiving a sensing signal from a sensor of the first surgical instrument in response to the sensor sensing a tag embedded in the first cannula when the sensor slides past the tag as the first surgical instrument is removed from the first cannula.

6. The method of claim 5, wherein generating the second configuration information comprises determining that the first surgical instrument transitions from the first state to the second state based on the sensing signal.

7. The method of claim 4, wherein the first sensing information indicates a first direction of movement of the first surgical instrument, and wherein the third sensing information indicates a second direction of movement of the first surgical instrument, wherein the second direction of movement is opposite of the first direction of movement.

8. The method of claim 4, wherein the second state is the initial state.

9. The method of claim 1, wherein the first surgical instrument is configured to relay the second sensing information from the second surgical instrument or the second cannula.

10. The method of claim 9, further comprising:

generating second configuration information of the second surgical instrument or the second cannula based on the first sensing information and the second sensing information, the second configuration information being used to configure the second surgical instrument or the second cannula to operate in a second state in which the second surgical instrument or the second cannula is operable with the first state of the first surgical instrument; and transmitting the second configuration information for the first surgical instrument to relay the second configuration information to the second surgical instrument or the second cannula to configure the second surgical instrument or the second cannula to operate in the second state.

11. The method of claim 1, wherein the first surgical instrument comprises an endoscope that is configured to perform one or more image processing operations while operating in the initial state, and is configured to perform one or more additional image processing operations or adjust at least one of the one or more image processing operations while operating in the first state.

12. The method of claim 1, wherein while operating in the initial state the first surgical instrument is powered on.

13. A surgical robotic system, comprising:

a first surgical instrument and a second surgical instrument;

at least one processor; and memory having instructions stored therein which when executed by the at least one processor causes the surgical robotic system to:

configure the first surgical instrument of the surgical robotic system such that the first surgical instrument operates in an initial state while the first surgical instrument is outside of and prior to being inserted into a first cannula of a trocar;

receive first sensing information from the first surgical instrument indicating that the first surgical instrument has been inserted into the first cannula;

receive second sensing information of the second surgical instrument or a second cannula; and responsive to receiving the first and second sensing information:

generate first configuration information of the first surgical instrument based on the first and second sensing information, the first configuration information being used to configure the first surgical instrument to operate in a first state corresponding to when the first surgical instrument is in the first cannula; and configure the first surgical instrument using the first configuration information such that the first surgical instrument operates in the first state different from the initial state, wherein the first configuration information is used to configure the first surgical instrument to operate in the first state in which the first surgical instrument is operable with the second surgical instrument or the second cannula.

14. The surgical robotic system of claim 13, wherein the instructions to receive the first sensing information from the first surgical instrument comprises:
   receiving a sensing signal from a sensor of the first surgical instrument in response to the sensor sensing a tag embedded in the first cannula when the sensor slides past the tag as the first surgical instrument is inserted into the first cannula.

15. The surgical robotic system of claim 14, wherein the instructions to generate the first configuration information comprises:
   determining that the first surgical instrument transitions from the initial state associated with the first surgical instrument being outside of the first cannula to the first state based on the sensing signal.

16. The surgical robotic system of claim 13, wherein the memory has further instructions to:
   receive third sensing information from the first surgical instrument indicating that the first surgical instrument is removed from the first cannula;
   generate second configuration information of the first surgical instrument based on the third sensing information, the second configuration information being used to configure the first surgical instrument to operate in a second state corresponding to when the first surgical instrument is outside of the first cannula; and
   transmit the second configuration information to the first surgical instrument to configure the first surgical instrument to operate in the second state.

17. The surgical robotic system of claim 16, wherein the instructions to receive the third sensing information from the first surgical instrument comprises:
   receiving a sensing signal from a sensor of the first surgical instrument in response to the sensor sensing a tag embedded in the first cannula when the sensor slides past the tag as the first surgical instrument is removed from the first cannula.

18. The surgical robotic system of claim 17, wherein the instructions to generate the second configuration information comprises determining that the first surgical instrument transitions from the first state to the second state based on the sensing signal.

19. The surgical robotic system of claim 16, wherein the first sensing information indicates a first direction of movement of the first surgical instrument, and wherein the third sensing information indicates a second direction of movement of the first surgical instrument, wherein the second direction of movement is opposite of the first direction of movement.

20. The surgical robotic system of claim 13,
   wherein the first surgical instrument is configured to relay the second sensing information from the second surgical instrument or the second cannula.

21. The surgical robotic system of claim 20, wherein the memory has further instructions to:
   generate second configuration information of the second surgical instrument or the second cannula based on the first sensing information and the second sensing information, the second configuration information being used to configure the second surgical instrument or the second cannula to operate in a second state in which the second surgical instrument or the second cannula is operable with the first state of the first surgical instrument; and
   transmit the second configuration information for the first surgical instrument to relay the second configuration information to the second surgical instrument or the second cannula to configure the second surgical instrument or the second cannula to operate in the second state.

* * * * *